United States Patent [19]

Rasberger et al.

[11] 4,380,515
[45] Apr. 19, 1983

[54] N-SUBSTITUTED 6-AMINO-DIBENZ[C,E][1,2]OXAPHOSPHORINES

[75] Inventors: Michael Rasberger; Samuel Evans, both of Riehen, Switzerland

[73] Assignee: Ciba-Geigy Corporation, Ardsley, N.Y.

[21] Appl. No.: 241,807

[22] Filed: Mar. 9, 1981

Related U.S. Application Data

[63] Continuation of Ser. No. 104,335, Dec. 17, 1979, abandoned, which is a continuation of Ser. No. 27,336, Apr. 5, 1979, abandoned.

[30] Foreign Application Priority Data

Apr. 14, 1978 [CH] Switzerland ............... 4026/78

[51] Int. Cl.³ .................. C07F 9/46; C07F 9/65
[52] U.S. Cl. .................. 260/936; 260/927 R; 544/157; 544/337
[58] Field of Search .................. 260/936, 927 R; 544/157, 337

[56] References Cited

U.S. PATENT DOCUMENTS 3,702,878 11/1972 Saito ..................... 260/936
3,887,655 6/1975 Shim ..................... 260/984
3,993,655 11/1976 Rasberger et al. ........... 260/45.8 R

FOREIGN PATENT DOCUMENTS 1256180 12/1971 United Kingdom ........... 260/936

Primary Examiner—Anton H. Sutto
Attorney, Agent, or Firm—Luther A. R. Hall

[57] ABSTRACT

Compounds of the formula I

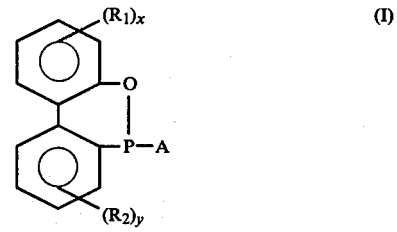

wherein
$R_1$ and $R_2$ independently of one another are substituted or unsubstituted hydrocarbon radicals, or halogen,
x and y independently of one another are 0, 1, 2 or 3, and
A is a substituted primary or secondary aliphatic or alicyclic, aromatic or araliphatic amine, in which the substituents are identical or different, a heterocyclic amine or a hydrazine derivative.

2 Claims, No Drawings

N-SUBSTITUTED 6-AMINO-DIBENZ[C,E][1,2]OXAPHOSPHORINES

This is a Continuation of application Ser. No. 104,335, filed on Dec. 17, 1979, now abandoned, which in turn is a Continuation of application Ser. No. 27,336, filed on Apr. 5, 1979, now abandoned.

The present invention relates to new N-substituted 6-amino-dibenz[c,e][1,2]oxaphosphorines, to the production thereof, to their use as stabilisers for organic material, and to the organic material stabilised by means of these compounds.

Phosphonites are known stabilisers, especially 6-phenoxy-dibenz[c,e][1,2]oxaphosphorine, which is described in the G.B. Pat. Specification No. 1,256,180. Although it is not specifically stated, it can be inferred from the same publication that 6-amino-dibenz[c,e][1,-2]oxaphosphorine could also be suitable as a stabiliser. However, these phosphonites do not meet the high requirements that a stabiliser should meet, particularly with respect to storage stability, water absorption, sensitivity to hydrolysis, processing stabilisation, colour behaviour, volatility, migration behaviour, compatibility and improved stability to light.

It was the object of the invention to provide stabilizers which do not have these disadvantages or have them to a lesser extent.

The present invention relates to N-substituted 6-amino-dibenz[c,e][1,2]oxaphosphorines of the formula (I)

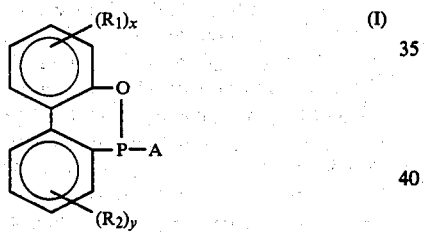

wherein
$R_1$ and $R_2$ independently of one another are substituted or unsubstituted hydrocarbon radicals, or halogen,
x and y independently of one another are 0, 1, 2 or 3, and
A is a substituted primary or secondary aliphatic or alicyclic, aromatic or araliphatic amine, in which the substituents are indentical or different, a heterocyclic amine or a hydrazine derivative.

As substituted or unsubstituted hydrocarbon radicals, $R_1$ and $R_2$ are in particular those having 1-8 C atoms, such as straight-chain or branched-chain alkyl having 1-8 C atoms, for example methyl, ethyl, iso-propyl, tertbutyl or tert-octyl; and as halogen they are in particular chlorine.

x is 0, 1, 2 or 3, preferably 0, 1 or 2, and especially 0.
y is 0, 1, 2 or 3, preferably 0.

A is a substituted primary or secondary amine in which the substituents are identical or different, which amine can contain up to six primary and/or secondary amino groups. Preferred compounds are those in which all primary or secondary amine nitrogen atoms occurring in the molecule are substituted with a group of the formula II:

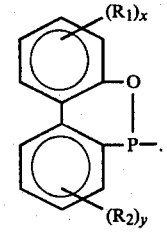

The symbols $R_1$, $R_2$, x and y in the formula II have the meanings given in the foregoing.

Of interest are in particular secondary amines, and above all branched-chain amines.

Preferred amines denoted by A are therefore those of the formula III

wherein
$R_3$ is hydrogen, $C_1$-$C_{22}$ alkyl, $C_2$-$C_{21}$ oxa- or thiaalkyl, $C_3$-$C_{18}$ alkenyl, $C_3$-$C_{18}$ alkynyl, $C_2$-$C_6$ hydroxyalkyl, $C_3$-$C_{24}$ alkoxycarbonylalkyl, $C_5$-$C_{12}$ cycloalkyl, $C_6$-$C_{14}$ aryl, $C_7$-$C_{15}$ alkaryl, $C_7$-$C_{15}$ aralkyl, a substituted or unsubstituted $C_5$-$C_{17}$ piperidin-4-yl group or a group of the formula II in which $R_1$, $R_2$, x and y have the meanings given above, and
$R_4$ is $C_1$-$C_{22}$ alkyl, $C_2$-$C_{21}$ oxa- or thiaalkyl, $C_3$-$C_{18}$ alkenyl, $C_3$-$C_{18}$ alkynyl, $C_2$-$C_6$ hydroxyalkyl, $C_3$-$C_{24}$ alkoxycarbonylalkyl, $C_5$-$C_{12}$ cycloalkyl, $C_6$-$C_{14}$ aryl, $C_7$-$C_{15}$ alkaryl, $C_7$-$C_{15}$ aralkyl, a substituted or unsubstituted $C_5$-$C_{17}$ piperidin-4-yl group, a group of the formula IV

or

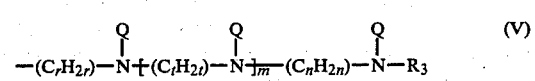

wherein
$R_3$ has the meaning given above,
n is 0 or 1,
$R_5$ is $C_2$-$C_{22}$ alkylene, $C_4$-$C_{22}$ alkenylene, $C_4$-$C_{22}$ alkynylene or $C_5$-$C_9$ cycloalkylene, each of which can be interrupted with one or two oxygen or sulfur atoms, or $R_5$ is a group of the formula VI

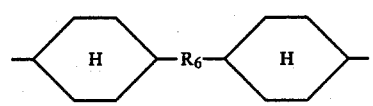

in which $R_6$ is —O—, —S— or —($R_7$)C($R_8$)—, wherein $R_7$ and $R_8$ independently of one another are hydrogen or $C_1$-$C_8$ alkyl, or $R_7$ and $R_8$ together with the C atom to which they are attached form $C_5$-$C_{12}$ cycloalkyl, or $R_7$ and $R_8$ together are 1,4-cyclohexylenedimethylene or 1,3,3-trimethylcyclohexylene-1,5, or $R_5$ is also phenylene, biphenylene or a group of the formula

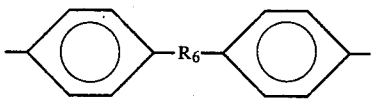

wherein $R_6$ has the meaning given above, and
r, t and n independently of one another are 2, 3, 4, 5 or 6, m is 0, 1, 2 or 3, Q is a group of the formula II, wherein $R_1$, $R_2$, x and y have the meanings given above, or $R_3$ and $R_4$ together with the N atom to which they are attached are also substituted pyrrolidine, oxazolidine, piperidine or morpholine, or $R_3$ and $R_4$ together form the radical —$CH_2$—$CH_2$—N(-Q)—$CH_2$—$CH_2$ wherein Q has the meaning given above.

If $R_3$ and $R_4$ are each $C_1$-$C_{22}$ alkyl, they can be methyl, ethyl, n-propyl, isopropyl, n-butyl, sec-butyl, tert-butyl, n-pentyl, n-hexyl, isohexyl, n-octyl, 1,1,3,3-tetramethylbutyl, n-nonyl, decyl, dodecyl, tetradecyl, hexadecyl, octadecyl, eicosyl or docosyl. As alkyl groups, $R_3$ and $R_4$ preferably contain 1-18 C atoms, with $R_3$ containing in particular 1-12 C atoms and $R_4$ in particular 1-4 C atoms. As $C_2$-$C_{21}$, essentially $C_4$-$C_{21}$, oxa- or thiaalkyl, $R_3$ and $R_4$ are preferably alkoxy- or alkylthiopropyl, such as butoxypropyl, dodecylthiopropyl, octyloxypropyl or octadecyloxypropyl.

As $C_3$-$C_{18}$ alkenyl, $R_3$ and $R_4$ are for example allyl, methallyl, n-hex-3-enyl, n-oct-4-enyl or n-undec-10-enyl. They are preferably allyl and methallyl but particularly allyl.

As $C_3$-$C_{18}$ alkynyl, $R_3$ and $R_4$ are for example propargyl, n-but-1-ynyl, n-but-2-ynyl or n-hex-1-ynyl. Alkynyl groups having 3 or 4 C atoms and particularly propargyl are preferred.

If $R_3$ and $R_4$ are each hydroxyalkyl having 1-6 C atoms, they can be 2-hydroxypropyl, 2-hydroxyethyl, 3-hydroxypropyl, 4-hydroxybutyl or 6-hydroxyhexyl.

If $R_3$ and $R_4$ are each $C_3$-$C_{24}$ alkoxycarbonylalkyl, preferably $C_3$-$C_{24}$ alkoxycarbonylmethyl or -ethyl and in particular $C_3$-$C_{14}$ alkoxycarbonylmethyl or $C_3$-$C_{15}$ alkoxycarbonylethyl, they can be for example methoxycarbonylmethyl, ethoxymethyl, methoxycarbonylethyl, octoxycarbonylmethyl, octoxycarbonylbutyl, dodecyloxycarbonylethyl or octadecyloxycarbonylethyl.

As $C_5$-$C_{12}$, preferably $C_5$-$C_8$ and especially $C_6$, cycloalkyl, $R_3$ and $R_4$ are for example cyclopentyl, cyclohexyl, cycloheptyl, cyclooctyl, cyclononyl or cyclododecyl.

As $C_6$-$C_{14}$ aryl, $R_3$ and $R_4$ are for example phenyl, α-naphthyl, β-naphthyl or phenanthryl. Phenyl groups are preferred.

If $R_3$ and $R_4$ are aralkyl having $C_7$-$C_{15}$ C atoms, they are for example benzyl, α-phenylethyl, α,α-dimethylbenzyl or 2-phenylethyl, preferably benzyl.

As $C_7$-$C_{15}$ alkaryl groups, $R_3$ and $R_4$ can be for example tolyl, 2,6-dimethylphenyl, 2,6-diethylphenyl, 2,4,6-triisopropylphenyl or 4-tert-butylphenyl.

If $R_3$ and $R_4$ are each $C_5$-$C_{17}$ piperidin-4-yl groups, they can be for example unsubstituted piperidin-4-yl, or the piperidine can be substituted by up to 5 alkyl groups, preferably by methyl or ethyl groups. Preferred substitution positions are the 2- and 6-position in the piperidine ring. They can also be 3,3,5-trimethyl-8-ethoxybicyclo[4,4,0]dec-2-yl.

$R_3$ and $R_4$ can therefore form piperidin-4-yl groups of the following structure

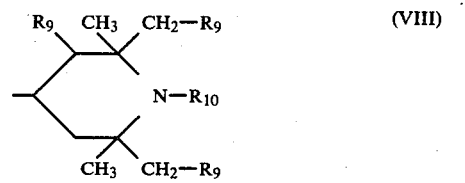

wherein $R_9$ is hydrogen or methyl, and $R_{10}$ is hydrogen, oxyl, $C_1$-$C_8$ alkyl, $C_3$-$C_8$ alkenyl, $C_3$-$C_6$ alkynyl, $C_7$-$C_{12}$ aralkyl, $C_2$-$C_{21}$ alkoxyalkyl, an aliphatic acyl group having 1-4 C atoms, or a group —$CH_2COOR_{11}$ where $R_{11}$ is $C_1$-$C_{12}$ alkyl, $C_3$-$C_8$ alkenyl, phenyl, $C_7$-$C_8$ aralkyl or cyclohexyl.

Very particularly preferred piperidin-4-yl groups are those wherein $R_9$ is hydrogen, and $R_{10}$ is hydrogen, methyl or acetyl.

The preferred meaning of $R_9$ is hydrogen.

As $C_1$-$C_{18}$ alkyl, $R_{10}$ is for example methyl, ethyl, n-propyl, n-butyl, n-pentyl, n-octyl, n-decyl, n-dodecyl or octadecyl. Preferred alkyl groups are those having 1 to 12 C atoms, especially those having 1 to 8 C atoms, in particular those having 1 to 4 C atoms, and above all methyl is preferred.

As $C_3$-$C_8$ alkenyl, $R_{10}$ is for example allyl, 3-methyl-2-butyl, 2-butenyl, 2-hexenyl or 2-octenyl, especially allyl.

As $C_3$-$C_6$ alkynyl, $R_{10}$ is for example propargyl.

As $C_7$-$C_{12}$ aralkyl, $R_{10}$ is for example benzyl, β-phenylethyl or 4-tert-butyl-benzyl, preferably benzyl.

If $R_{10}$ is alkoxyalkyl, the alkyl moiety can contain 1 to 3 C atoms, and the alkoxy moiety can consist of 1 to 18 C atoms, for example in methoxymethyl, ethoxymethyl, 2-methoxyethyl, 2-ethoxyethyl, 2-n-butoxyethyl, 3-n-butoxypropyl, 2-octoxyethyl or 2-octadecyloxyethyl. To be particularly mentioned are compounds in which $R_{10}$ is an alkoxyalkyl group having 2 to 6 C atoms.

As an aliphatic acyl group having 1 to 4 C atoms, $R_{10}$ is for example formyl, acetyl, acryloyl or crotonoyl, especially acetyl.

If $R_{10}$ is the group —$CH_2COOR_{11}$, $R_{11}$ as $C_1$-$C_{12}$ alkyl is for example methyl, ethyl, isopropyl, n-butyl, isobutyl, tert-butyl, isopentyl, n-octyl or n-dodecyl. Preferably $R_{11}$ is $C_1$-$C_4$ alkyl. As $C_3$-$C_8$ alkenyl, $R_{11}$ is for example allyl, 2-butenyl or 2-hexenyl. As $C_7$-$C_8$ aralkyl, $R_{11}$ is for example benzyl or α-phenylethyl.

If $R_3$ is a group of the formula II, this group preferably has the same substitution as the dibenz[c,e][1,2]oxaphosphorin-6-yl group already present in the molecule.

If $R_3$ and $R_4$ with the N atom to which they are attached form a pyrrolidine, oxazolidine, piperidine or morpholine ring, these heterocycles can be substituted by up to five methyl or ethyl groups. These ring systems are preferably unsubstituted.

The symbol n can be 0 or preferably 1.

As $C_2$-$C_{22}$ alkylene, preferably $C_2$-$C_9$ and particularly $C_2$-$C_6$ alkylene, $R_5$ can be for example dimethylene, trimethylene, tetramethylene, hexamethylene, octamethylene, nonamethylene, 2,2,4-trimethylhexamethylene, decamethylene, dodecamethylene, octadecamethyl or docosamethylene. If the alkylene groups are interrupted by —O— or —S—, they can be 2-thiapropylene-1,3,3-thiapentylene-1,5,4-oxahep-
tamethylene or 3,6-dioxaoctylene-1,8.

If $R_5$ is $C_4$–$C_{22}$ alkenylene or alkynylene, it is for
example 2-butenylene-1,4,2-butynylene-1,4,2,4-hexadii-
nylene-1, or propenylene-1,3.

As $C_5$–$C_9$ cycloalkylene, $R_5$ is for example 1,2-cyclo-
pentylene, 1,2-cyclohexylene, 1,3-cyclohexylene, 1,4-
cyclohexylene, 1,4-cycloheptylene or 1,2-cyclonony-
lene. As cycloalkylene, $R_5$ preferably has 6 C atoms.

$R_7$ and $R_8$ as $C_1$–$C_8$ alkyl are for example ethyl, n-pro-
pyl, isopropyl, n-butyl, n-phenyl, n-hexyl or n-octyl. As
alkyl groups, $R_7$ and $R_8$ are preferably however methyl.

With the C atom to which they are attached, $R_7$ and
$R_8$ can also form $C_5$–$C_{12}$ cycloalkyl, preferably cyclo-
hexyl. It can be cyclopentyl, cyclohexyl, cycloheptyl,
cyclooctyl or cyclododecyl.

Independently of one another, r, t and n are 2, 3, 4, 5
or 6; they are preferably however identical, and are in
particular 2 or 3.

m can be 0, 1, 2 or 3. Preferably m is 0 or 1, but partic-
ularly 0.

If radicals Q are present in the compounds, these are
preferably substituted in the same way as the other
dibenz[c,e][1,2]oxaphosphorin-6-yl groups present in
the molecule.

Preferred compounds of the formula I are those
wherein
$R_1$ is $C_1$–$C_8$ alkyl,
x is 0, 1 or 2,
y is 0,
A is a group —N($R_3$)$R_4$ (III), wherein
$R_3$ is hydrogen, $C_1$–$C_{18}$ alkyl, $C_3$–$C_4$ alkenyl, $C_3$–$C_4$
  alkynyl, $C_3$–$C_{24}$ alkoxycarbonylmethyl or -ethyl,
  $C_5$–$C_{12}$ cycloalkyl, phenyl, benzyl, $C_7$–$C_{15}$ alkaryl,
  a substituted or unsubstituted $C_5$–$C_{17}$ piperidin-4-yl
  group, or a group of the formula II, wherein $R_1$, x
  and y have the meanings given above,
$R_4$ is $C_1$–$C_{18}$ alkyl, $C_3$–$C_4$ alkenyl, $C_3$–$C_4$ alkynyl,
  $C_3$–$C_{24}$ alkoxycarbonylmethyl or -ethyl, $C_5$–$C_{12}$
  cycloalkyl, phenyl, benzyl, $C_7$–$C_{15}$ alkaryl, a sub-
  stituted or unsubstituted $C_5$–$C_{17}$ piperidin-4-yl
  group, a group of the formula IV or V, wherein $R_3$
  has the meaning given above,
n is 0 or 1,
$R_5$ is $C_2$–$C_9$ alkylene which can be interrupted with
  one or two oxygen or sulfur atoms, or it is cyclo-
  hexylene, or a group of the formula VI, wherein
$R_6$ is —O—, —S— or —($R_7$)C($R_8$)—, wherein
$R_7$ and $R_8$ independently of one another are hydrogen
  or methyl, or
$R_7$ and $R_8$ together with the C atom to which they are
  attached form cyclohexylene, or
$R_7$ and $R_8$ together are 1,4-cyclohexylenedimethylene
  or 1,3,3-trimethyl-cyclohexylene-1,5,
r, t and n are 2 or 3,
m is 0 or 1,
Q is a group of the formula II, wherein $R_1$, x and y
  have the meanings given above, or
$R_3$ and $R_4$ together with the N atoms to which they
  are attached form a pyrrolidine, oxozolidine, piper-
  idine or morpholine ring, or
$R_3$ and $R_4$ together are the radical —CH$_2$CH$_2$—N(-
  Q)—CH$_2$CH$_2$—, wherein Q has the meaning given
  above.

Of interest are compounds of the formula I wherein x
and y are 0,
A is a group —N($R_3$)$R_4$ (III), wherein $R_3$ hydrogen, $C_1$–$C_{18}$ alkyl, allyl, propargyl, $C_3$–$C_{14}$
  alkoxycarbonylmethyl, $C_3$–$C_{15}$ alkoxycar-
  bonylethyl or $C_5$–$C_8$ cycloalkyl,
$R_4$ is $C_1$–$C_4$ alkyl, allyl, propargyl, $C_3$–$C_{14}$ alkoxycar-
  bonylmethyl, $C_3$–$C_{15}$ alkoxycarbonylethyl, $C_5$–$C_8$
  cycloalkyl, or a group of the formula IV or V,
  wherein $R_3$ has the meaning given above,
n is 1,
$R_5$ is $C_2$–$C_6$ alkylene,
r, t and n are 2 or 3,
m is 0,
Q is a group of the formula II, wherein x and y have
  the meanings given above, or
$R_3$ and $R_4$ together with the N atom to which they are
  attached form a piperidine or morpholine ring, or
$R_3$ and $R_4$ together are the radical —CH$_2$CH$_2$—N(-
  Q)—CH$_2$CH$_2$—, wherein Q has the meaning given
  above.

Particularly preferred are compounds of the formula
I wherein
x and y are 0,
A is a group —N($R_3$)$R_4$ (III), wherein
$R_3$ is hydrogen, $C_1$–$C_{12}$ alkyl or cyclohexyl,
$R_4$ is $C_1$–$C_4$ alkyl, cyclohexyl, or a group of the for-
  mula IV, wherein $R_3$ has the meaning given above,
  and Q is a group of the formula II, wherein x and y
  have the meanings given above,
n is 1,
$R_5$ is $C_2$–$C_6$ alkylene,
$R_3$ and $R_4$ together with the N atom to which they are
  attached form a piperidine or morpholine ring, or
$R_3$ and $R_4$ together are the radical —CH$_2$CH$_2$—N(-
  Q)—CH$_2$CH$_2$— wherein Q has the meaning given
  above.

Examples of compounds of the formula I are:
(1) 6-(N,N-di-n-octylamino)-dibenz[c,e][1,2]oxaphos-
  phorine,
(2) 6-(2'-aza-3',3',5'-trimethyl-8'-ethoxy-bicyclo-
  [4,4,0]dec-2'-yl)-dibenz[c,e][1,2]oxaphosphorine,
(3) 6-(N-2',6'-dimethylphenyl-N-cyclohexyl-amino)-
  dibenz[c,e][1,2]oxaphosphorine,
(4) 6-(N-cyclododecyl-N-tert-octyl-amino)-dibenz[-
  c,e][1,2]oxaphosphorine,
(5) 6-(N-tert-butylamino)-dibenz[c,e][1,2]oxaphos-
  phorine,
(6) 6-(N-2',6'-dimethylphenylamino)-dibenz[c,e][1,-
  2]oxaphosphorine,
(7) 6-(N-octadecylamino)-dibenz[c,e][1,2]oxaphos-
  phorine,
(8) 6-(N-cyclododecylamino)-dibenz[c,e][1,2]oxa-
  phosphorine,
(9) 6-(N-p-tert-octylphenyl-N-isopropylamino)-
  dibenz[c,e][1,2]oxaphosphorine,
(10) 6-(N-cyclohexyl-N-allyl-amino)-dibenz[c,e][1,-
  2]oxaphosphorine,
(11) 2,2-bis-[4'-[N-(dibenz[c,e][1'',2'']oxaphosphorin-
  6''-yl)]-amino-cyclohexyl]-propane,
(12) N,N'-bis-(dibenz[c,e][1,2]-2,4-di-tert-butyloxa-
  phosphorin-6-yl)-benzidine,
(13) N,N'-bis-(dibenz[c,e][1,2]oxaphosphorin-6-yl)-
  N,N'-dicyclopentyl-hexamethylenediamine,
(14) N,N'-bis-(dibenz[c,e][1,2]oxaphosphorin-6-yl)-
  N,N'-di-isopropyl-hydrazine,
(15) N,N'-bis-(dibenz[c,e][1,2]oxaphosphorin-6-yl)-
  N,N'-di-(1'-isopropyl-2'-methyl-propyl)e-
  thylenediamine,
(16) N,N'-bis-(dibenz[c,e][1',2']oxaphosphorin-6-yl)-
  4,9-dioxadodecylenediamine,

(17) N,N'-bis-(dibenz[c,e][1,2]oxaphosphorin-6-yl)-N,N'-dicycloheptyl-hexamethylenediamine,
(18) 1,4-bis-(dibenz[c,e][1',2']oxaphosphorin-6'-yl)-2,5-dimethylpiperazine,
(19) 1,4-bis-[N-(dibenz[c,e][1',2']oxaphosphorin-6'-yl)-aminopropyl]-piperazine,
(20) N,N'-N"-tris-(dibenz[c,e][1,2]-2-methyl-oxaphosphorin-6-yl)-diethylenetriamine,
(21) N,N-bis-[3-[N'-(dibenz[c,e][1',2']oxaphosphorin-6'-yl)]-aminopropyl]-N-(dibenz[c,e][1",2"]oxaphosphorin-6"-yl)-amine,
(22) N,N-bis-(dibenz[c,e][1,2]oxaphosphorin-6-yl)-N-n-butylamine,
(23) N,N'-bis-dibenz[c,e][1,2]oxaphosphorin-6-yl)-N,N'-diisopropyl-hydrazine,
(24) N-cyclohexyl-N-(dibenz[c,e][1,2]-2,4-dichlorooxaphosphorin-6-yl)-aminosuccinic acid-dioctyl ester,
(25) Q-N(cyclohexyl)-(CH$_2$)$_3$—N(Q)—(CH$_2$)$_3$—N(Q)—(CH$_2$)$_3$—N(Q)—(CH$_2$)$_3$—N(cyclohexyl)Q, and
(26) Q—N(H)—[CH$_2$—CH$_2$—N(Q)]$_4$—CH$_2$—CH$_2$—N(H)Q.

In the formulae 25 and 26, Q denotes the group (dibenz[c,e][1,2]oxaphosphorin-6-yl):

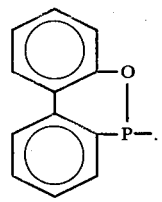

The phosphonites of the formula I can be produced by methods known per se, particularly by amidation or transamidation reactions, for example by reacting a phosphonite of the formula VI

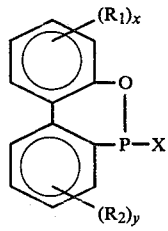

wherein X is a reactive group, and R$_1$, R$_2$, x and y have the meanings given above, with an amine of the formula VII

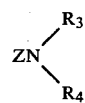

wherein Z is hydrogen or an Na, Li or K atom, and R$_3$ and R$_4$ have the meanings given above.

A reactive group x is for example halogen, particularly chlorine, alkoxy, phenoxy or a primary or secondary amino group.

The reaction can be performed in a manner known per se, for example at −5° C. to 80° C., or by heating, preferably to above 80° C., for example 80°–170° C. The reaction can be performed without or in the presence of an inert solvent, such as aprotic solvents, for example ligroin, toluene, xylene, hexane, cyclohexane, dimethylformamide, dimethylacetamide, sulfolane, acetonitrile, dioxane, di-n-butyl ether, 1,2-dichloroethane, dimethylsulfoxide, ethyl acetate, methyl ethyl ketone, nitrobenzene, nitromethane, tetrahydrofuran, chloroform or trichloroethylene. If X is halogen, the reaction is preferably carried out in the presence of a base, such as sodium carbonate, or an amine, for example triethylamine, pyridine or N,N-dimethylaniline. If is however quite possible to perform the reaction with an excess of amine of the formula VII, with this acting as an acid acceptor. Amine bases used in excess can simultaneously act as solvent.

The starting materials of the formulae VI and VII are known, or, where they are new, they can be produced by methods analogous to known methods. The phosphonites of the formula VI have been described for example in the G.B. Patent Specification No. 1,256,180, whilst the starting amines of the formula VII are compounds which have been known for a long time and which are in many cases commercial products.

The compounds of the formula I can be used according to the present invention as stabilisers for plastics and elastomers to protect these from damage caused by the action of oxygen, light and heat. Examples of plastics concerned are the polymers listed in the German Offenlegungsschrift No. 2,456,864 on pages 12–14.

Suitable substrates are for example:
1. Polymers which are derived from mono-unsaturated hydrocarbons, such as polyolefins, for example low density and high density polyethylene, which can be crosslinked, polypropylene, polyisobutylene, polymethylbut-1-ene and polymethylpent-1-ene.
2. Mixtures of the homopolymers mentioned under 1, for example mixtures of polypropylene and polyethylene, of polypropylene and polybut-1-ene and of polypropylene and polyisobutylene.
3. Copolymers of the monomers on which the homopolymers mentioned under 1 are based, such as ethylene/propylene copolymers, propylene/but-1-ene copolymers, propylene/isobutylene copolymers and ethylene/but-1-ene copolymers, and also terpolymers of ethylene and propylene with a diene, for example hexadiene, di-cyclopentadiene or ethylidenenorbornene.
4. Polystyrene and its copolymers, such as SAN, ABS, IPS, ASA, and EP-modified styrene copolymers.
5. Polyamides.
6. Linear polyesters.
7. Polyurethanes.
8. Polycarbonates.
9. Elastomers, such as polybutadiene, SBR, polyisoprene, polychloroprene and nitrile rubber.
10. Thermoplastic elastomers, such as SBS, SIS and S-EP-S.
11. Polyvinyl chloride and the like.

The present invention relates also to a process for stabilising polymers against thermooxidative degradation during production, isolation, processing and use, which process comprises incorporating into the polymer at least one compound of the formula I.

The compounds of the formula I are incorporated into the substrates at a concentration of 0.005 to 5 percent by weight, calculated relative to the material to be stabilised.

Preferably 0.01 to 1.0 percent by weight, and particularly preferably 0.02 to 0.5 percent by weight, of the compunds, relative to the material to be stabilised, is incorporated into this material. Incorporation is effected for example by mixing at least one of the compounds of the formula I, and optionally further additives, by methods customary in the art, into the polymer either before or during shaping, or alternatively by application of the dissolved or dispersed compounds to the polymers, optionally with subsequent removal of the solvent by evaporation.

The new compounds can also be added in the form of a masterbatch, which contains these compounds for example at a concentration of 2.5 to 25 percent by weight, to the plastics to be stabilised.

In the case of crosslinked polyethylene, the compounds are added before crosslinking.

The invention relates therefore also to the plastics which are stabilised by the addition of 0.01 to 5 percent by weight of a compound of the formula I, and which can optionally contain further additives. The plastics stabilised in this manner can be used in the widest variety of forms, for example as films, fibres, tapes or profiles, or as binders for lacquers, adhesives or putties.

Examples of further additives which can be used together with the stabilizers according to the invention are: antioxidants, UV absorbers and light stabilisers, such as 2-(2'-hydroxyphenyl)-benzotriazoles, 2,4-bis-(2'-hydroxyphenyl)-6-alkyl-s-triazines, 2-hydroxybenzophenones, 1,3-bis-(2'-hydroxybenzoyl)-benzenes, esters of substituted or unsubstituted benzoic acids and acrylates, and also nickel compounds, sterically hindered amines, oxalic acid diamides, metal deactivators, phosphites, compounds which destroy peroxide, polyamide stabilisers, basic Co stabilisers, nucleating agents or other additives, for example plasticisers, lubricants, emulsifiers, fillers, carbon black, asbestos, kaolin, talc, glass fibres, pigments optical brighteners, flameproofing agents and antistatic agents.

The invention is further illustrated by the following Examples.

EXAMPLE 1

6-(N,N-Di-cyclohexyl-amino)-dibenz[c,e][1,2]oxaphosphorine 35.1 g (0.15 mol) of 6-chloro-dibenz[c,e][1,2]oxaphosphorine, 27.1 g (0.15 mol) of dicyclohexylamine and 50 ml of triethylamine are kept at reflux temperature for 10 hours. Toluene is added to the solution; the triethylamine hydrochloride is then removed by filtration, and the filtrate is concentrated in vacuo. The crystalline product has a melting point of 162° C. (Compound I).

EXAMPLE 2

If the procedure is carried out as described in Example 1 except that 15.1 g (0.15 mol) of diisopropylamine is used instead of dicyclohexylamine, there is obtained 6-(N,N-di-isopropyl-amino)-dibenz[c,e][1,2]oxaphosphorine having a melting point of 111° C. (Compound II).

EXAMPLE 3

By using the molar equivalent of cyclohexylamine and two molar equivalents of 6-chloro-dibenz[c,e][1,2]oxaphosphorine, under otherwise the same conditions as those described in Example 1, there is obtained N,N-bis-(dibenz[c,e][1,2]oxaphosphorin-6-yl)-N-cyclohexylamine having a melting point of 191° C. (Compound III).

The following compounds are produced under otherwise the same conditions as those described in Example 1:

EXAMPLES 4–12

4. 6-[N-(2,6-di-isopropyl)-anilino]-dibenz[c,e][1,2]oxaphosphorine, m.p. 50° C.;
5. N,N'-bis-(dibenz[c,e][1,2]oxaphosphorin-6-yl)-piperazine, m.p. 250° C.;
6. N,N'-bis-(dibenz[c,e][1,2]oxaphosphorin-6-yl)-N-(2-ethyl)-hexylamine, m.p. 125° C.;
7. N,N-bis-(dibenz[c,e][1,2]oxaphosphorin-6-yl)-N-dodecylamine, viscous oil: calculated: C 74.3, H 7.2, N 2.4, P 10.6; found: C 74.2, H 7.3, N 2.3, P 10.3;
8. N,N,N',N'-tetra(dibenz[c,e][1,2]oxaphosphorin-6yl)N,N'-hexamethylenediamine;
9. 6-[N,N-di-(2,2,6,6-tetramethylpiperidin-4-yl)-amino]-dibenz[c,e][1,2]oxaphosphorine, m.p. 214° C.;
10. 6-[N-dodecyl-N-(2,2,6,6-tetramethylpiperidin-4-yl)-amino]-dibenz[c,e][1,2]oxaphosphorine, m.p. 50° C.;
11. N,N-bis-(dibenz[c,e][1,2]oxaphosphorin-6-yl)-amine, m.p. 184°–185° C.; and
12. N,N,N-tris-(dibenz[c,e][1,2]oxaphosphorin-6-yl)-amine, m.p. 260° C.

EXAMPLE 13

100 parts of unstabilised polyethylene of high density having a molecular weight of about 500,000 ("Lupolen 5260 Z" in powder form, BASF), are mixed dry with 0.1 and 0.05 part, respectively, of the phosphonites shown in Table 1 below. The mixtures are kneaded in a Brabender plastograph at 220° and at 50 revolutions per minute. During this time, the kneading resistance is continuously recorded as a turning moment. As a result of crosslinking of the polymer, there occurs in the course of kneading a rapid increase in the turning moment after an initial period of constant value. The effectiveness of the stabilisers is manifested by a lengthening of the time in which this value remains constant.

TABLE 1

| Parts of phosphonite | Time in minutes until the turning moment changes |
| --- | --- |
| none | 2 |
| 0.1 part of compound I | 22 |
| 0.05 part of compound I | 15 |
| 0.1 part of compound II | 22 |
| 0.05 part of compound II | 15½ |

What is claimed is:

1. A compound of the formula

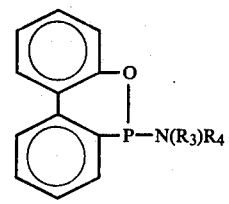

wherein
  $R_3$ is hydrogen, $C_1$–$C_{12}$ alkyl, cyclohexyl or the group Q, where Q is

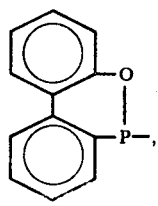

$R_4$ is $C_1$-$C_{12}$ alkyl, cyclohexyl or a group of the formula

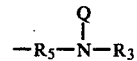

where
$R_3$ and Q have the meanings given above,
$R_5$ is $C_2$-$C_6$ alkylene,
$R_3$ and $R_4$ together with the N atom to which they are attached form a piperidine or morpholine ring, or
$R_3$ and $R_4$ together are the radical —CH$_2$CH$_2$—N(Q)—CH$_2$CH$_2$— wherein Q has the meaning given above.

2. 6-(N,N-Di-isopropyl-amino)-dibenz[c,e][1,2]oxaphosphorine, according to claim 1.

* * * * *